US007248708B2

(12) United States Patent
Vaudrey et al.

(10) Patent No.: US 7,248,708 B2
(45) Date of Patent: Jul. 24, 2007

(54) NOISE CANCELING MICROPHONE

(75) Inventors: Michael A. Vaudrey, Blacksburg, VA (US); William R. Saunders, Blacksburg, VA (US)

(73) Assignee: Adaptive Technologies, Inc., Blacksburg, VA (US)

( * ) Notice: Subject to any disclaimer, the term of this patent is extended or adjusted under 35 U.S.C. 154(b) by 0 days.

(21) Appl. No.: 11/170,553

(22) Filed: Jun. 29, 2005

(65) Prior Publication Data

US 2006/0002570 A1 Jan. 5, 2006

Related U.S. Application Data

(63) Continuation of application No. 09/970,356, filed on Oct. 3, 2001, now Pat. No. 6,963,649.

(60) Provisional application No. 60/242,952, filed on Oct. 24, 2000.

(51) Int. Cl.
*H04B 15/00* (2006.01)
*A61F 11/06* (2006.01)
*G10L 19/00* (2006.01)

(52) U.S. Cl. .................... 381/94.7; 381/71.1; 381/94.1; 704/200.1

(58) Field of Classification Search ............... 381/94.7, 381/94.1, 71.1; 704/200.1; 379/406.12, 379/406.13, 406.08
See application file for complete search history.

(56) References Cited

U.S. PATENT DOCUMENTS 4,649,505 A * 3/1987 Zinser et al. .......... 379/406.08
5,559,839 A * 9/1996 Doelman .................... 375/350
5,796,819 A * 8/1998 Romesburg ............ 379/406.09
5,815,496 A * 9/1998 Flanagan et al. ........... 370/287
6,608,897 B1 * 8/2003 Jin et al. ............... 379/406.09

* cited by examiner

*Primary Examiner*—Vivian Chin
*Assistant Examiner*—Devona E. Faulk
(74) *Attorney, Agent, or Firm*—Roberts Mardula & Wertheim, LLC

(57) ABSTRACT

An improved noise canceling microphone is provided including robust design features and advanced noise control and speech discrimination convergence characteristics. Two adaptive controllers are used to ensure robust performance in quickly changing acoustic environments ensuring an acceptable minimum performance characteristic. Additionally, a new real-time spectral estimation procedure is applied to a noise canceling communications microphone platform that permits continued and optimal adaptation of non-voice bandwidth frequencies during speech transients.

31 Claims, 6 Drawing Sheets

NOISE CANCELING MICROPHONE

RELATIONSHIP TO OTHER APPLICATIONS

This application is a continuation of U.S. application Ser. No. 09/970,356, filed Oct. 3, 2001 now U.S. Pat. No. 6,963,649, which application is incorporated by reference for all purposes and from which priority is claimed.

BACKGROUND

The following paragraphs provide some background and prior art information in order to illustrate the specific characteristics of noise canceling microphones that are improved by this invention. Prior inventions have failed to provide for design robustness and the wide noise suppression bandwidth required for clear communication in high ambient noise fields. This invention focuses on providing a new noise canceling microphone using controller and algorithmic features that drastically improve the performance over the prior art noise canceling microphones. This application relies on the provisional Patent Application Ser. No. 60/242,952 filed Oct. 24, 2000, with inventors Michael Vaudrey and William Saunders entitled “Improved Noise Canceling Microphone”.

To review the nominal field being considered, it is recalled that passive noise canceling microphones typically incorporate a single membrane to sense ambient sound, where the housing of that membrane is open to the environment on both sides. Far-field sounds impact the membrane (essentially) equally on both sides, generating no net movement, and thus a low sensitivity. Near field sounds (such as when the microphone is placed close to a speaker’s mouth) cause the membrane to move more significantly in one direction than another, causing a higher sensitivity. This higher sensitivity to close-range voice versus lower sensitivity to far-field ambient noise, provides a low frequency improvement in the signal-to-noise ratio because of the associated far field noise rejection; thus improving low frequency speech intelligibility. There are a multitude of patents that cover the passive noise canceling microphone concept in various ways including: U.S. Pat. Nos. 4,258,235, 3,995,124, 5,329,593, and 5,511,130 among others. The microphone invention described here is an active microphone and is therefore different from this prior art regarding passive elements.

A second category of noise canceling microphones will be referred to as active noise canceling microphones. The most rudimentary active noise canceling microphones perform identically to the passive noise canceling microphones mentioned above. The structural difference is that an active element such as a subtraction circuit is employed in order to electronically difference two microphone signals, in order to generate the noise canceled output signal. The two microphones are positioned facing away from each other, where one is directed toward the desired signal source, or speaker’s mouth. There are patents focusing on the use of active elements in creating a noise canceling microphone including U.S. Pat. Nos. 5,303,307 and 5,511,130. The algorithms and design features presented herein are not anticipated by any of this prior art.

More advanced implementations of noise canceling microphones have arisen as a result of increased DSP processing capabilities, the present invention included. These adaptive active noise cancellation microphones typically include the use of an adaptive filter as part of the active canceling element and provide improved performance over both the passive and active noise canceling microphones. The invention disclosed herein is significantly different from the prior art in this area as evidenced below.

U.S. Pat. No. 5,917,921 by Sasaki et. al. is a very general embodiment of an adaptive active noise canceling microphone. Sasaki uses an adaptive filter with two microphone signals to reduce the noise in one of those signals, using the other as a reference input to the adaptive filter. The inventive elements described in the present invention are not described or anticipated by the disclosure of Sasaki, which only focuses on the general idea of using an adaptive filter with two microphones for the purpose of reducing wind noise. The specific embodiments described by this invention are not anticipated by Sasaki.

U.S. Pat. No. 5,953,380 by Ikeda focuses on a very specific method for controlling the convergence parameter of the adaptation process as a function of the two input signals. A complex series of delays and power estimations creates a single convergence parameter for the time domain adaptive filter. This single convergence parameter is varied with the detection of the speech, as determined by the “SN power ratio estimation”. Ikeda does not anticipate the present inventions because the need for robust performance in a physical product is not discussed; nor does Ikeda anticipate the concept of multiple frequency-dependent convergence parameters or the use of frequency-domain adaptive control.

U.S. Pat. No. 5,978,824, also by Ikeda, is an adaptive filtering method for creating a “clean” estimate of the noise as well as a “clean” estimate of the desired signal. The two adaptive filters create estimates of the desired signal and the noise signal, which are independently used to generate convergence parameters for the two adaptive filters. The two adaptive filters used in Ikeda’s invention are used to a) generate a more accurate estimate of the signal to noise at any given time and b) create more accurate estimates of the speech, as well as the noise. The two adaptive filters used in the present invention provide an entirely different effect focused on improving robustness during quickly changing ambient noise disturbances; in addition, the arrangement of the adaptive filters in the present invention is completely different from and is not anticipated by Ikeda.

U.S. Pat. No. 5,473,684 by Bartlett and Zuniga describes two first-order differential microphones that are used to create an adaptive second-order differential microphone. The present invention uses two omni-directional microphones to create a single, adaptive, first-order differential microphone. The use of omni-directional microphones simplifies the physical construction of the microphone assembly, since both transducer backplanes can remain secured in the housing. (FOD microphones must be open on both sides in order to be effective). No mention by Bartlett is made concerning the use of two adaptive filters for optimizing the robust control of ambient noise. In addition, no mention is made of using a frequency domain adaptive algorithm for controlling multiple convergence parameters of individual frequencies.

U.S. Pat. No. 5,473,702 by Yoshida et al. controls the adaptation of the adaptive noise-canceling filter by adjusting the convergence parameter as a function of the error signal. There are several options that are discussed through a complex rule-based system that ultimately decides when the algorithm should temporarily cease adaptation. Frequency domain control of adaptation is not anticipated by Yoshida, nor is the use of two adaptive filters for robust performance of a two-element adaptive noise canceling microphone design.

Finally, U.S. Pat. No. 5,319,736 by Hunt describes a digital signal processing system that creates a frequency spectrum of speech from noisy speech to be used by a speech recognition system. This system does not anticipate using multiple adaptive filters as disclosed herein. In addition, Hunt's system does not anticipate performing real-time frequency domain adaptive filtering for communication microphone applications. Instead the output of his system is used as an input to a frequency domain vocoder.

In summary, this review of the prior art in adaptive noise canceling microphones directly points to the need for a more robust design of an adaptive noise-canceling microphone where the minimum performance is at least as good as passive noise canceling microphones at all times and the maximum performance can far exceed that of the existing noise canceling microphones. Tests have shown that in highly reverberant environments, the passive noise control microphone design can perform better than the prior art adaptive noise canceling microphones discussed above, if safeguards are not applied. The dual-filter embodiment of this invention disclosed herein is such a safeguard that ensures the adaptive noise canceling microphone will always perform at least as well as the passive version, thereby improving the robustness of any noise canceling microphone previously described in the prior art.

The second failing of the prior adaptive noise canceling microphone designs is that fast variations in the noise field cannot be tracked when the adaptive filter has a small convergence coefficient. This problem leads to increased average noise levels for the adaptive filter arrangements discussed by others. The first-stage, single-weight adaptive filter of the present invention eliminates the degradation associated with fast tracking of noise field variations.

Finally, the prior art does not anticipate the need for frequency domain adaptation. This is a problem for all of those previously discussed inventions because the adaptation of the entire filter is halted at every frequency every time there is a component of speech detected. This leads to sub-optimal wideband noise suppression. The solution offered by the present invention is to only adapt individual frequency bins, allowing non-speech, noise frequencies to be adapted while simultaneously halting adaptation for those frequency bins dominated by speech content. Detailed descriptions of the invention are provided next.

SUMMARY

The invention disclosed as embodiments herein improves the performance of existing adaptive noise canceling microphone designs. The first improvement (which can be used simultaneously with the second) uses dual adaptive filters. The first adaptive filter acts as a single-weight gain calibrator to equalize two omni-directional microphones so that their subtraction is optimized to minimize the error output. Because this is only a single element adaptive filter, the output is the same as a tuned active noise canceling microphone, but achieved with minimal algorithmic complexity. The second adaptive filter is then used to perform the broadband noise control, focused primarily on high frequency ambient attenuation. The second design improvement creates an automatically adjustable convergence parameter for each frequency bin in the spectrum. Since speech formants can be tonal in nature, it is advantageous to continue to adapt components of the spectrum that do not contain speech, even during speech segments. By performing the adaptive filtering in the frequency domain, each weight update can be independently controlled by adjusting its respective convergence parameter.

DETAILED DESCRIPTION

Figure 6:
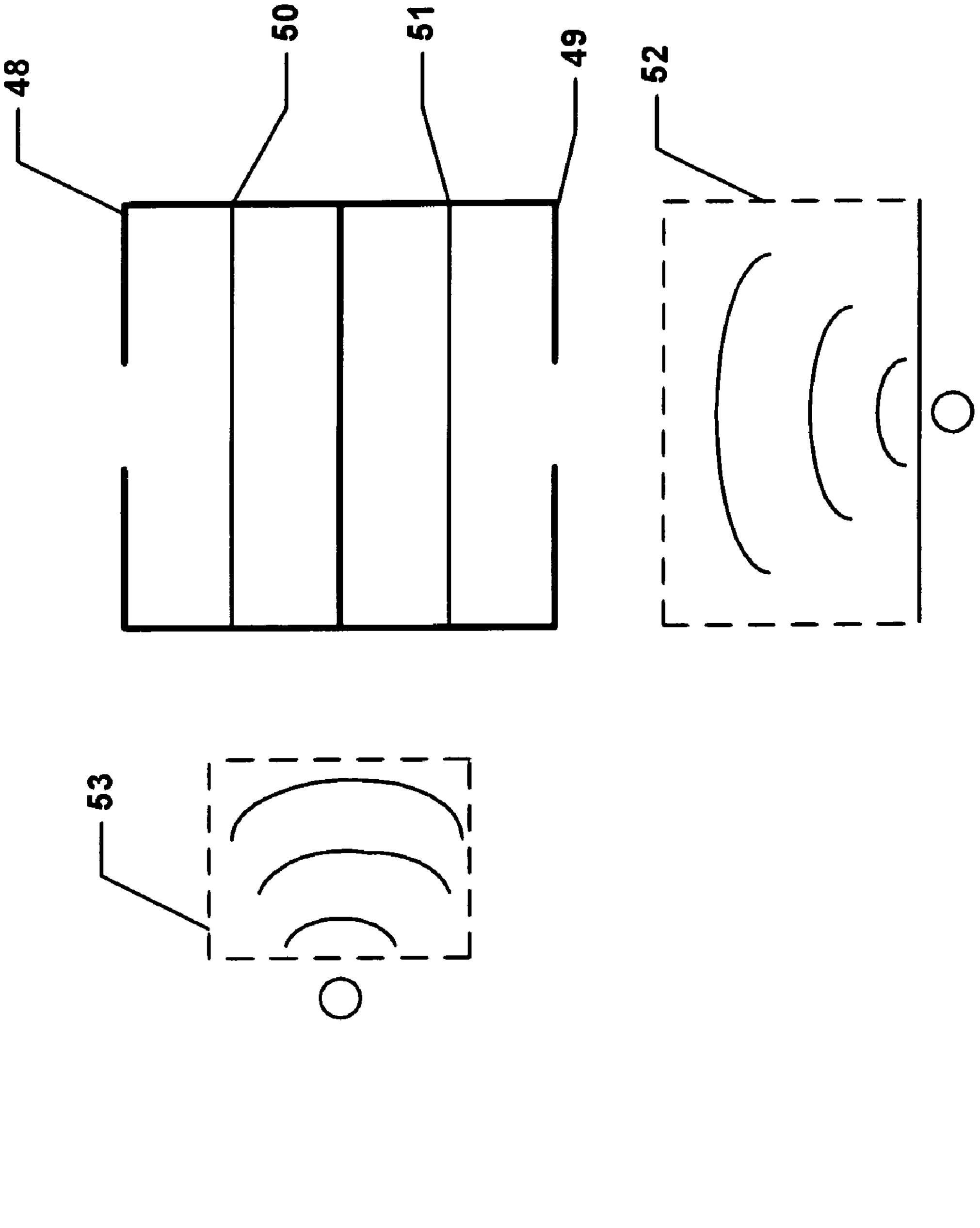
FIG. 6 is a depiction of two omni-directional microphones situated as a active noise canceling microphone.

The first critical component of this invention is the microphone architecture. It is more advantageous from a performance and implementation standpoint, to use two omni-directional microphones situated as shown in FIG. 6. Bartlett et. al. in (U.S. Pat. No. 5,473,684) discussed the use of two first-order differential microphones to form a second-order differential microphone. Structurally, this is a difficult assembly to construct since both microphones must have the back and front open to the acoustic environment. This increases the distance between the membranes thereby decreasing high frequency coherence between the two microphones. As coherence decreases, performance of the adaptive feedforward controller also decreases. Therefore, it is essential to this invention that the transducer unit consists of two omni-directional microphones. Referring again to FIG. 6, the first omni-directional microphone (49) is situated close to the speaker's mouth or the desired source (52) while the second microphone (48) is facing 180 degrees away from the first Assuming the microphones are identical and have equal sensitivities, the amplitude of the voice (52) will be greater as measured by the close microphone diaphragm (51) than the amplitude measured by the second microphone diaphragm (50). Alternatively, the amplitude of the ambient noise (53) will be measured nearly equally by both diaphragms. Using omni directional microphones as in (48 and 49), the backs of the elements remain closed and can therefore be placed directly adjacent to each other in the microphone housing. This closer proximity serves to increase the broadband coherence between the two microphones, thereby improving the noise attenuating performance as compared to previous inventions. Furthermore, omni-directional microphones have a nearly flat frequency response, ensuring accurate reproduction of both the noise and the speech for improved low frequency control performance. This configuration of two omni-directional microphones is used throughout the remainder of this discussion where the reference signal (adaptive filter input) is the microphone facing away from the speaker and the communication microphone is facing toward the speaker's mouth.

Figure 1:
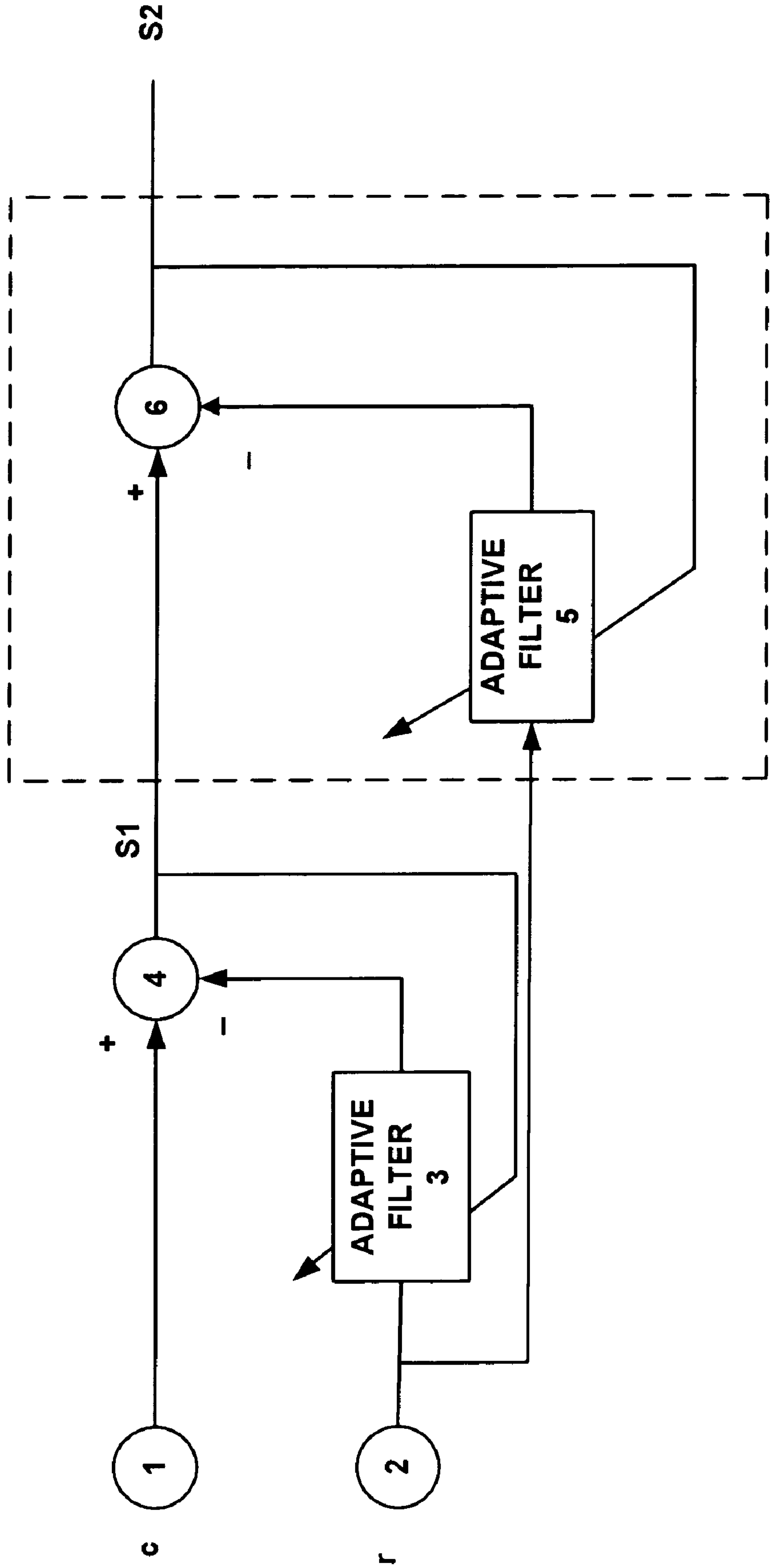
FIG. 1 is a block diagram of a general implementation of a dual adaptive filter for a noise canceling microphone that ensures a minimal performance equal to that of a passive noise canceling microphone.

The first part of this invention can be understood clearly by examining FIG. 1. There are two omni-directional microphones (1 and 2) that detect two different signals (c and r respectively) in the physical arrangement specified above.

When ambient noise in the environment is detected by the microphones, it is detected almost equally by both the 1 and 2 microphones (so that c=r). However, when the person speaks, since microphone 1 is closer to the mouth, microphone 1 has a higher amplitude of speech than microphone 2, even though both microphones also are continuing to detect the ambient noise at similar levels. A simple subtraction of microphone 1 from microphone 2 represents the concept of an active noise canceling microphone where the difference results in more speech than noise (since the noise content is approximately the same on both microphones). When using two omni directional microphones, a simple subtraction may not be sufficient for exact cancellation of the noise signal. This may be due to the microphones having slightly different sensitivities, an obstruction, or a variation in preamplifier hardware characteristics. It is therefore necessary to incorporate a variable gain in order to compensate for these variations.

In general, the variations in omni-directional microphones will not be frequency dependent, but rather gain related. Therefore, the adaptive filter (3) will be implemented using a single weight, w, to control the gain variations between microphone 1 and 2. The resulting signal is:

$$s.sub.1=c-w*r$$

where, $$w.sub.k+1=w.sub.k+mu*r*s.sub.1$$

and the subscript on the adaptive weight refers to the iteration number. After a sufficient number of iterations transpire, the signal s.sub.1 will be minimized by the gain w. The resulting signal, s.sub.1, is equivalent to that of an optimized active noise canceling microphone. However, the difference is that the tuning of the relative gain between microphone 1 and 2 is performed automatically by the adaptive filter.

Continuing on with FIG. 1 and the embodiment description, s.sub.1 is used as the error signal to the next adaptive stage enclosed by the dotted line in the right side of FIG. 1. The microphone 2 signal is used as the reference signal in the second adaptive filter (5). This adaptive filter is designed to have as many weights as is practical for the particular DSP implementation and desired bandwidth (typically up to 4 kHz for speech). This adaptive filter performs an optimal minimization of the signal s.sub.2 by subtracting (6) any of the noise in signal s.sub.1 remaining from the first adaptive process. Before the specific advantages are noted, FIG. 2 illustrates one further detail that is disclosed as part of this invention.

Each adaptive filter operates on the premise of minimizing its respective error signal. During moments when the speaker is active (speaking), the optimal solution to minimizing the error must change to compensate for the new direction of the "noise" source. In fact, we do not want to cancel the voice, only the noise. Therefore, it is required that we prevent adaptation of the adaptive filter during time segments when voice is present. In order to instantaneously identify those time segments in real time, we need only to look at the output power of the error signal (output of 4, 6 or 7). FIG. 2 illustrates the method that is disclosed for controlling adaptation as a function of the voice. The output of the adaptive filter (8) is subtracted from (7) the input signal to create the error signal that is used to update the adaptive filter. During periods of quiet, this error signal is minimized below a certain level threshold (11). The error signal is continuously compared (10) to the fixed threshold value (11) and if it is below the threshold then adaptation continues as determined by a switch (9) that controls the convergence parameter mu in the adaptive weight update to be some nonzero constant "a". If the error signal instantly rises above the threshold, then the comparator signals the switch (9) to set the convergence parameter to zero, ceasing adaptation on the speech. (Optimizing this operation as a function of frequency is discussed as the second part of this invention in subsequent paragraphs).

Figure 2:
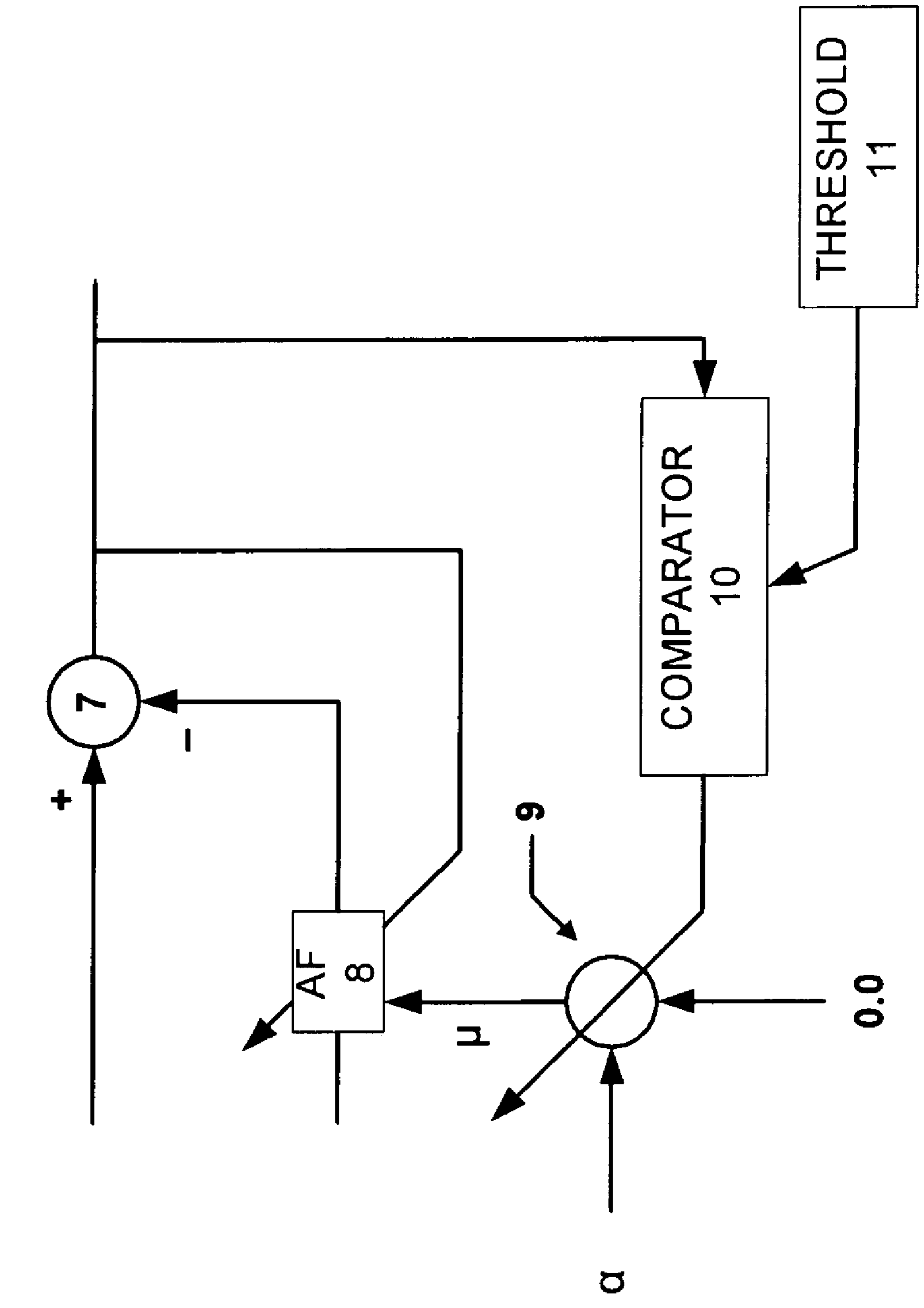
FIG. 2 is a block diagram of an instantaneous convergence control of an adaptive filter in response to controller output power.

The process of FIG. 2, where the convergence parameter controls update of the adaptive filter as a function of the presence of voice, is required in order to prevent cancellation of the voice signal by the adaptive filter. It should be noted that prior art does not disclose a method for controlling the convergence parameter strictly as an instantaneous function of the error signal used by the adaptive filter. FIG. 1 illustrates the first exemplary embodiment of this invention. Incorporating the convergence control of FIG. 2 into each of the adaptive filters (3 and 5) of FIG. 1, a distinct advantage over the prior art is seen. The method of controlling the convergence rate instantaneously increases the response time of the adaptive filter to speech transients, as well as reduces computational load that is seen when incorporating an average or mean calculation over a period of time.

If the prior art adaptive noise canceling microphone is tested in noise environments having high reverberation times, it will be seen that the overall noise reduction performance can be less than that of a simple passive noise canceling microphone. This is due to the fact that the coherence between two microphones in a highly reverberant environment can be less than that in an anechoic environment. The performance of an adaptive filter in a feedforward control arrangement is a direct function of the coherence between the reference and the disturbance measurement. The new dual adaptive filter arrangement shown in FIG. 1 solves this problem. By using a single weight adaptive filter and subtracting the reference (r) from the communication microphone (c), the exact performance of the passive noise canceling microphone is achieved as the signal s.sub.1. At this point, regardless of the coherence between the signal s.sub.1 and r (determining the performance of the second adaptive stage), we can be assured that the minimum performance achieved will be at least equal to that of the passive noise canceling microphone. (Note that the single weight adaptive filter is less dependent on the broadband coherence between r and c, and primarily focuses on the very low frequency coherence which is typically high even in reverberant environments). In certain cases, the second adaptive filter (5) may offer no performance and s.sub.2 will be equal to s.sub.1, which is precisely the performance of the passive (or tuned active) noise canceling microphone.

This invention provides a new level of robustness in the adaptive noise canceling microphone design that is not anticipated by any of the prior art. This invention ensures that the worst (adaptive) performance that can be expected is no less than that of a passive noise canceling microphone. It should be emphasized that the first adaptive filter is only a single weight and acts as a calibration gain to optimally match the levels between c and r to minimize the mean squared error. Larger adaptive filters (3) in the calibration location will suffer the same difficulty in suppressing noise as (5) if the coherence is too low between the inputs.

As noted earlier, the successful adaptation of (3) relies on the coherence between the signals at (1) and (2). There may be instances when it is advantageous to only adapt the first adaptive filter (3) of FIG. 1 for a short time before fixing the calibration gain (3) because of poor coherence between the two inputs. This can be easily accomplished by using a timer that sets the convergence parameter mu to zero after a specified period of time. This ensures that the communication signal used in the second adaptive stage of FIG. 1 (enclosed by dotted line) is always equal in performance to that of a fixed active noise canceling microphone, while still having the benefit of having a correlated reference signal. It should be noted that this configuration is not possible via Bartlett's invention (U.S. Pat. No. 5,473,684) because he uses two first-order differential microphones. It should also be noted that omni-directional microphones are much more convenient to implement (physically) since their backs can remain closed. This improves their local proximity to one another because they can be situated directly adjacent to each other. In highly reverberant fields this is a distinct advantage for high frequency control since there is a higher coherence between the signals, the closer the microphones get. Therefore, for the optimal positioning of FIG. 6, the configuration of FIG. 1 is the only way to provide a minimum of passive noise canceling performance using two omni-directional microphones in an adaptive controller.

A further improvement in noise canceling microphone performance derives from the use of frequency domain adaptive filtering (FDAF). FDAF is a method for designing adaptive filters and adaptive controllers that performs the weight update in the frequency domain. The adaptive noise canceling microphone is a particularly suitable application for FDAF because of the inherent dependence on frequency domain characteristics of both the speech and noise. In general, the ambient noise to be canceled by a noise canceling microphone will usually be broadband or random in nature. Speech elements can be very narrowband, or at times broadband. As mentioned earlier, it is desirable to cease adaptation of the adaptive filter during times when there is speech so it is not canceled. FIG. 2 illustrated one possible way to perform this switching adaptation as a function of output power for a single convergence parameter.

All prior art implementations of such a convergence parameter have focused on time domain control. When using the LMS algorithm in the time domain, only a single convergence parameter can be used. If a vector of convergence parameters were proposed for the time domain LMS algorithm, there would be no logical way to control their state. Further, since prior art has only proposed time domain signal power control, all of these methods cease adaptation of the ENTIRE adaptive filter each time the signal power exceeds a certain threshold. It should be clear that since speech can be narrowband in its spectral content, it is not necessary to stop adaptation of the ENTIRE adaptive filter, but only the parts that are affected by the speech signal itself. Therefore, it is clear that this frequency domain implementation of the convergence parameter offers improved performance opportunities.

Frequency dependent convergence as described here is impossible to accomplish in the time domain. Therefore the invention disclosed next is to provide a frequency domain adaptive filter used in a unique adaptive noise canceling microphone arrangement so that individual segments of the noise bandwidth can continue to adapt while the segments of the speech bandwidth are fixed during speech. This is accomplished using the microphone and algorithm construction shown in FIGS. 3 and 4.

Figure 3:
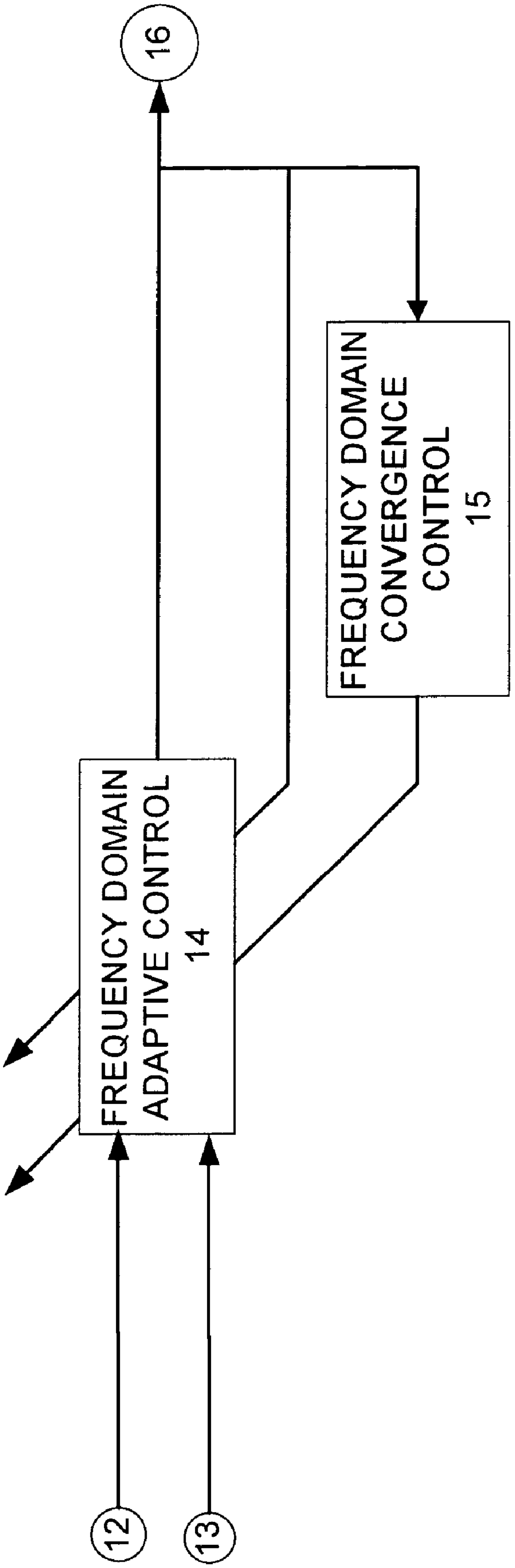
FIG. 3 is a general depiction of a frequency domain adaptive controller and its associated convergence control

FIG. 3 is a general block diagram showing two microphone signals (12 and 13) entering the frequency domain adaptive controller 14 that generates the output 16. The output is the cleaned speech signal or error signal to be minimized. As with the time domain structure, the convergence of the adaptive filter is controlled by selectively turning off the convergence parameter mu as a function of the output power of the adaptive controller. This is accomplished generally through the frequency domain convergence control (15). As mentioned earlier, the primary difference (and key advantage) here is that the convergence can be controlled as a function of frequency.

Figure 4:
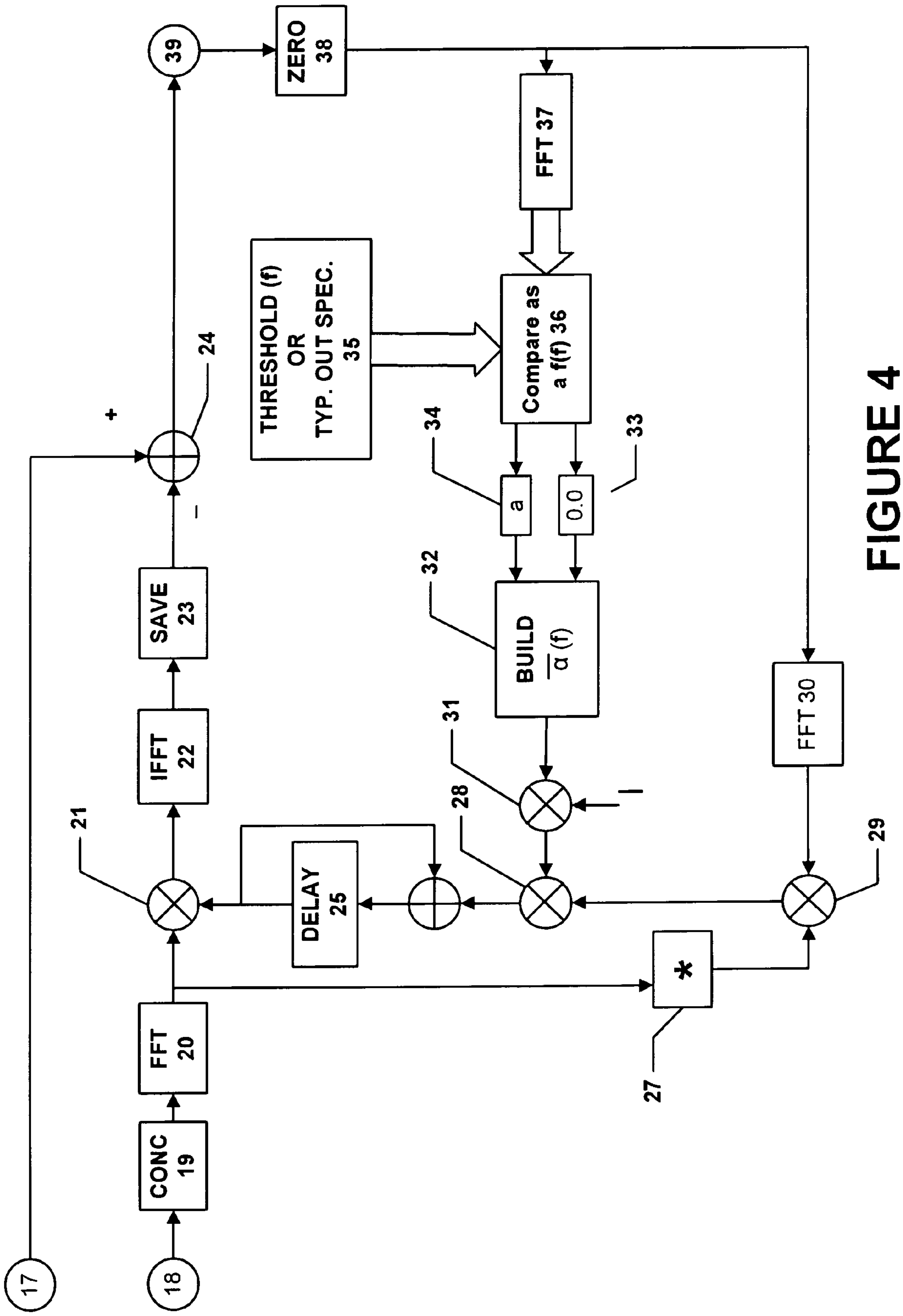
FIG. 4 is a specific implementation of the frequency domain adaptive controller and the frequency dependent convergence control.

FIG. 4 illustrates a more detailed implementation of FIG. 3 in an unconstrained frequency domain adaptive filtering format. The communication microphone signal (17) has the control signal (output of 23) subtracted from it in the time domain to produce the output (or error) signal 39. To perform the adaptive filtering operation in the frequency domain, care must be taken to prevent circular convolution. It should be noted that FIG. 4 illustrates circular correlation in the computation of the weight update and is therefore known as unconstrained adaptation. The inventive feature is the control of the convergence parameters. To prevent circular convolution during the filtering operation in the frequency domain, two block sizes are concatenated with each other (19) before the fast Fourier transform (20) is taken of the reference input. This reference is then multiplied (21) by the adaptive filter weights in the frequency domain to create a filter output that is inverse fast Fourier transformed (22) and appropriate samples are taken as the block output (23). The output or error signal (39) is concatenated with appropriate zero padding before the FFT (30) is taken and the correlation is computed (29) for the weight update.

A critical part of this invention enters at the multiplication (28) of the convergence parameters by the correlation of the tap input vector and the error signal. The convergence parameters are formed as a function of frequency and stored in a vector alpha.sub.13 bar (32). This is accomplished by first taking the FFT (37) of the instantaneous error signal (39). The power in EACH of the spectral bins of this FFT is then compared (36) to either one of two stored vectors. The first possibility is a manually entered predetermined set of magnitude threshold values (as a function of frequency) that represent the controlled spectral bins of the noise level of signal 39 when no speech is present. The second possibility is that the controlled spectrum is stored during a time when no speech is present, which represents a typical controlled output spectrum. Either vector (which is a threshold magnitude as a function of frequency) should contain nearly the same values. On a frequency bin-by-bin basis, the magnitude of the output of (37) is compared (36) with the stored magnitude of (35) the threshold values and a decision is made to choose either 34 or 33. This comparison operation is typically accomplished through a "if" statement in a software code, but can also be implemented using FFT and comparator hardware components. If the magnitude of the actual signal (output of 37) in a bin is greater than the stored threshold (35) in that same bin, then there is speech in that bin and the convergence parameter for that bin (vector location) is chosen to be zero (33). Likewise, if the actual bin measurement is lower than the stored threshold, a nonzero adaptation constant "a" (34) is chosen for that respective element of the vector alpha.sub.13 bar. After each frequency is examined, the vector alpha.sub.13 bar will consist of a series of zeros and nonzero constants "a", where the zeros reside in all spectral bins whose magnitude was greater than the stored threshold values. This vector is then multiplied by the identity matrix (31) and the result is multiplied (28) by the correlation. Finally, the current and future (25, 26) frequency domain weights are computed and multiplied by the input tap vector (21). These steps are repeated each time a new input and error block is accumulated.

It should be clear from the above discussion that the convergence parameters can vary within one iteration as a function of frequency. This is a critical advantage over the prior art, because adaptation of the filter can continue in bins that do not have speech in them. In particular, it is unusual to have speech formants at frequencies below 200 Hz for most speaking voices. Therefore, it is possible, using the invention presented above to continue to adapt frequencies between 0 and 200 Hz during an entire conversation. This is not possible using a single, time domain convergence parameter. If noise in frequencies below 200 Hz (or in other frequency bins not containing speech) changes during the course of a conversation, the adaptive filter will not be able to adapt with a single convergence parameter because the signal power will indicate that speech is present and will continue to prevent adaption. However, using the frequency domain approach described herein, convergence on non-speech frequencies can occur during speech without adapting the speech itself.

Figure 5:
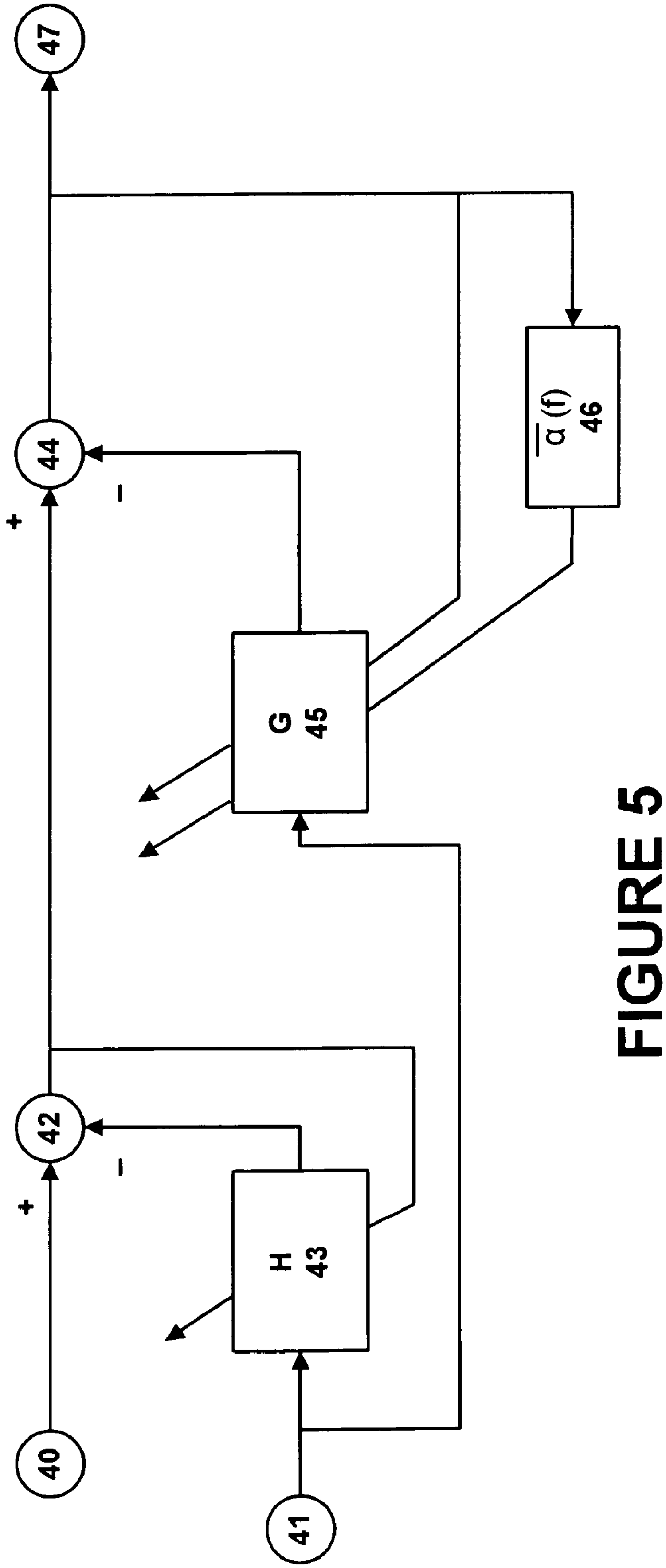
FIG. 5 is a block diagram of the combination of dual adaptive filtering and frequency domain adaptive filtering.

As mentioned earlier, it is advantageous to combine both the improvements discussed above to form a third embodiment that provides both robust and optimized control for the dual omni-directional noise canceling microphone. FIG. 5 illustrates a block diagram of the combined system incorporating the robust property of creating a passive noise microphone minimal performance (43) with the improved frequency adaptive filtering (45) and convergence control (46) discussed above. The reference microphone (41) after being filtered by the single weight adaptive filter (43) is subtracted from the communication microphone to form the minimal performance of the simple active (or passive) noise control microphone. The signal is then used as the communication (or error) signal in the frequency domain adaptive filter scheme (45) discussed in detail above. As before, the convergence parameters are computed (46) as a function of the spectral power of the output (47) as compared to a stored threshold for each frequency bin.

Having described the invention it is readily apparent that many changes and modifications thereto may be made by those of ordinary skill in the art without departing from the scope of the appended claims.

What is claimed is:

1. An adaptive noise canceling microphone system comprising:

a first microphone for generating a first microphone signal containing primarily speech and noise;

a second microphone for generating a second microphone signal containing primarily noise;

a first adaptive filter comprising a single filter coefficient wherein the first adaptive filter is adapted to:

generate a first output signal from the second microphone signal; and generate a first error signal, wherein the first error signal is generated by subtracting the first output signal from the first microphone signal;

a second adaptive filter comprising multiple filter coefficients, wherein the second adaptive filter is adapted to:

generate a second output signal from the second microphone signal; and generate a second error signal, wherein the second error signal is generated by subtracting the second output signal from the first error signal: and first and second adaptive convergence controllers, wherein the first adaptive convergence controller is adapted to change a rate of convergence of the first adaptive filter based on the first error signal and the second adaptive convergence controller is adapted to change a rate of convergence of the second adaptive filter based on the second error signal.

2. The system as in claim 1, wherein the first adaptive convergence controller comprises a gain comparator and a switch connected thereto and wherein the gain comparator is adapted to:

determine whether the first error signal exceeds a predetermined threshold; if first error signal exceeds a predetermined threshold, then send the switch a switching signal; and wherein the switch is adapted to:

receive the switching signal; and in response to the switching signal, set a convergence parameter of the first adaptive filter to zero.

3. The system as in claim 1, wherein the second adaptive convergence controller comprises a gain comparator and a switch connected thereto and wherein the gain comparator is adapted to:

determine whether the second error signal exceeds a predetermined threshold;

if second error signal exceeds a predetermined threshold, then send the switch a switching signal; and wherein the switch is adapted to:

receive the switching signal; and in response to the switching signal, set a convergence parameter of the second adaptive filter to zero.

4. The system as in claim 1 wherein the system further comprises a timer and wherein the timer is adapted to set a convergence parameter of the first adaptive filter to zero after a predetermined control period following inception of control.

5. The system as in claim 1 wherein the first microphone is directed toward a speaker's mouth and the second microphone is simultaneously directed away from the speaker's mouth.

6. The system as in claim 1 wherein adaptive convergence controller is implemented using software.

7. The system as in claim 1 wherein the adaptive convergence controller is implemented using hardware.

8. An adaptive noise canceling microphone control method comprising:

generating at a first microphone a first microphone signal containing primarily speech and noise;

generating at a second microphone a second microphone signal containing primarily noise;

generating a first output signal by filtering the second microphone signal with the first adaptive filter;

generating a first error signal by subtracting the first output signal from the first microphone signal;

sending the first error signal to a first convergence controller;

generating a second output signal by filtering the second microphone signal with the second adaptive filter;

generating a second error signal by subtracting the second output signal from the first error signal;

sending the second error signal to a second convergence controller;

changing a rate of convergence of the first adaptive filter based on the first error signal; and setting a second convergence parameter changing a rate of convergence of the second filter based on the second error signal.

9. The control method as in claim 8, wherein the method further comprises:

establishing when the first adaptive filter initiates control;

determining whether a predetermined control period has elapsed since the first adaptive filter initiated control; and if the predetermined control period has elapsed, setting a convergence parameter of the first adaptive filter to zero.

10. The system as in claim 8, wherein the convergence controller is implemented using software.

11. The system as in claim 8, wherein the convergence controller is implemented using hardware.

12. The system as in claim 8, wherein the first microphone is directed toward a speaker's mouth and the second microphone is simultaneously directed away from the speaker's mouth.

13. An adaptive noise canceling microphone control system comprising:

a first microphone, wherein the first microphone generates a first microphone signal containing primarily speech and noise, a second microphone, wherein the second microphone generates a second microphone signal containing primarily noise, a single-weight adaptive filter having a single filter coefficient, wherein the single weight adaptive filter is adapted to:

generate a first output signal from the second microphone signal; and generate a first error signal, wherein the first error signal is generated by a frequency domain controller comprising a series of stored frequency domain threshold values each associated with a frequency; and a frequency domain adaptive filter having multiple filter coefficients, wherein the frequency domain adaptive filter is adapted to:

generate a second output signal from the second microphone signal; and generate a second error signal, wherein the second error signal is generated by subtracting the second output signal from the first error signal, wherein the first error signal is used to update the first adaptive filter, and the second error signal is used to update the frequency domain adaptive filter, and wherein the second error signal represents primarily speech;

a gain comparator adapted to: determine whether the first error signal exceeds any one of the series of stored frequency domain threshold values; and if the first error signal exceeds any one of the series of stored frequency domain threshold values, then send the switch a switching signal for the frequency associated with the one of the series of stored frequency domain threshold values; and a switch, wherein the switch is adapted to:

receive the switch signal; and

In response to the switch signal, set a convergence parameter of the single-weight adaptive filter to zero.

14. The system as in claim 13, wherein the series of stored frequency domain threshold values is stored based on user desired threshold levels.

15. The system as in claim 13, wherein the series of stored frequency domain threshold values is determined by calculating a Fourier transform of the first error signal during a moment in time when no speech is present in the first microphone signal and the Fourier transform of the first error signal is stored as the threshold values.

16. The system as in claim 13, wherein the frequency domain controller is implemented using software.

17. The system as in claim 13, wherein the frequency domain controller is implemented using hardware.

18. The system as in claim 13, wherein the first microphone is directed toward a speaker's mouth and the second microphone is simultaneously directed away from the speaker's mouth.

19. An adaptive noise canceling microphone control method comprising:

generating at a first microphone a first microphone signal containing primarily speech and noise generating at a second microphone a second microphone signal containing primarily noise, generating a first output signal at a first adaptive filter from the second microphone signal;

generating a second output signal at a second adaptive filter from the second microphone signal, generating a first error signal by subtracting the first output signal from the first microphone signal;

generating a second error signal by subtracting the second output signal from the first error signal;

comparing at a frequency domain comparator a Fourier transform of the second error signal to a set of frequency domain threshold values;

selecting a first convergence parameter for controlling a rate of convergence of the first adaptive filter based on the first error signal; and selecting a set of second convergence parameters for controlling a rate of convergence of the second adaptive filter based on the set of frequency domain threshold values.

20. The control method as in claim 19, wherein the set of frequency domain threshold values are stored based on user desired threshold levels.

21. The control method as in claim 19, wherein determining a magnitude threshold value for a frequency bin comprises calculating the FFT of the first output signal when no speech is present in the first microphone signal.

22. The control method as claim 19, wherein comparing at a frequency domain comparator the Fourier transform of the second error signal to a set of frequency domain threshold values comprises:

defining frequency bins, wherein a frequency bin comprises a range of frequencies within a spectrum and is associated with a magnitude threshold value, a power measure value, and a convergence parameter value;

determining a magnitude threshold value for a frequency bin, wherein the magnitude threshold value is indicative of a signal level of the first output signal when no speech is present; and determining a power measure value for a frequency bin by taking a fast Fourier transform (FFT) of the first output signal; and wherein, selecting a series of convergence parameters comprises:

comparing the power measure value in the frequency bin to the threshold value in the frequency bin;

if the power measure in the frequency bin is greater than the magnitude threshold value in the bin, then assigning the convergence parameter a value of zero; and if the power measure in the frequency bin is less than or equal to the magnitude threshold value in the bin, then assigning the convergence parameter a non-zero value.

23. The control method as claim 19, wherein the frequency domain comparator is implemented using software.

24. The control method as claim 19, wherein the frequency domain comparator is implement using hardware.

25. The system as claim 19, wherein the first microphone is directed toward the speaker's mouth and the second microphone is simultaneously directed away from the speaker's mouth.

26. An adaptive noise canceling microphone system comprising:

a first microphone for generating a first microphone signal containing primarily speech and noise;

a second microphone for generating a second microphone signal containing primarily noise;

a first adaptive filter comprising:

a single filter coefficient wherein the first adaptive filter is adapted to: generate a first output signal from the second microphone signal; and generate a first error signal, wherein the first error signal is generated by subtracting the first output signal from the first microphone signal;

a gain comparator and a switch connected thereto and wherein the gain comparator is adapted to:

determine whether the first error signal exceeds a predetermined threshold;

if first error signal exceeds a predetermined threshold, then send the switch a switching signal; and wherein the switch is adapted to:

receive the switching signal; and in response to the switching signal, set a convergence parameter of the first adaptive filter to zero; and a second adaptive filter comprising multiple filter coefficients, wherein the second adaptive filter is adapted to:

generate a second output signal from the second microphone signal; and generate a second error signal, wherein the second error signal is generated by subtracting the second output signal from the first error signal; and first and second adaptive convergence controllers, wherein the first adaptive convergence controller is adapted to control the rate of convergence of the first adaptive filter and the second adaptive convergence controller is adapted to control the rate of convergence of the second adaptive filter.

27. The system as in claim 26, wherein the second adaptive convergence controller comprises a gain comparator and a switch connected thereto and wherein the gain comparator is adapted to:

determine whether the second error signal exceeds a predetermined threshold;

if second error signal exceeds a predetermined threshold, then send the switch a switching signal; and wherein the switch is adapted to:

receive the switching signal; and in response to the switching signal, set a convergence parameter of the second adaptive filter to zero.

28. The system as in claim 26, wherein the system further comprises a timer and wherein the timer is adapted to set a convergence parameter of the first adaptive filter to zero after a predetermined control period following inception of control.

29. The system as in claim 26, wherein the first microphone is directed toward a speaker's mouth and the second microphone is simultaneously directed away from the speaker's mouth.

30. The system as in claim 26, wherein adaptive convergence controller is implemented using software.

31. The system as in claim 26, wherein the adaptive convergence controller is implemented using hardware.

* * * * *

UNITED STATES PATENT AND TRADEMARK OFFICE

CERTIFICATE OF CORRECTION

PATENT NO. : 7,248,708 B2
APPLICATION NO. : 11/170553
DATED : July 24, 2007
INVENTOR(S) : Michael A. Vaudrey and William R. Saunders It is certified that error appears in the above-identified patent and that said Letters Patent is hereby corrected as shown below:

Column 1, line 10, insert the following section title and paragraph, before the section entitled "Background":

-- GOVERNMENT RIGHTS

This invention was made with Government support under contract N0421-03-C-0009 awarded by the Department of the Navy. The Government has certain rights in this invention. The U.S. Government has a paid-up license in this invention and the right in limited circumstances to require the patent owner to license others on reasonable terms as provided by the terms of contract N0421-03-C-0009 awarded by the Department of the Navy. --

Signed and Sealed this

Seventeenth Day of November, 2009

David J. Kappos
*Director of the United States Patent and Trademark Office*